United States Patent
Asano

(10) Patent No.: US 8,133,739 B2
(45) Date of Patent: Mar. 13, 2012

(54) REAGENT FOR MEASUREMENT OF CONCENTRATION OF LEAD, AND METHOD FOR MEASUREMENT OF CONCENTRATION OF LEAD

(75) Inventor: Takaharu Asano, Tsukuba (JP)

(73) Assignee: Kowa Co., Ltd., Nagoya-shi (JP)

( * ) Notice: Subject to any disclaimer, the term of this patent is extended or adjusted under 35 U.S.C. 154(b) by 15 days.

(21) Appl. No.: 12/669,572

(22) PCT Filed: Jul. 18, 2008

(86) PCT No.: PCT/JP2008/001923
§ 371 (c)(1),
(2), (4) Date: Jan. 19, 2010

(87) PCT Pub. No.: WO2009/013884
PCT Pub. Date: Jan. 29, 2009

(65) Prior Publication Data
US 2010/0184234 A1    Jul. 22, 2010

(30) Foreign Application Priority Data
Jul. 20, 2007   (JP) ................................. 2007-189601

(51) Int. Cl.
*G01N 21/00* (2006.01)
(52) U.S. Cl. .......................................... 436/77; 436/164
(58) Field of Classification Search ............... 436/77, 436/164
See application file for complete search history.

(56) References Cited

U.S. PATENT DOCUMENTS

| | | |
|---|---|---|
| 6,437,067 B1 | 8/2002 | Asano et al. |
| 6,515,089 B1 | 2/2003 | Asano et al. |
| 2006/0078832 A1 | 4/2006 | Gore et al. |
| 2008/0299664 A1 | 12/2008 | Asano et al. |
| 2009/0263907 A1 | 10/2009 | Asano et al. |

FOREIGN PATENT DOCUMENTS

| | | |
|---|---|---|
| EP | 1 574 531 A1 | 9/2005 |
| EP | 1 729 126 A1 | 12/2006 |
| JP | 2004 37430 | 2/2004 |
| JP | 2006 242691 | 9/2006 |
| WO | 2006 011549 | 2/2006 |

OTHER PUBLICATIONS

An Optical Sensor for the Detection of Heavy Metal Ions R. Czolk, J. Reichert, and H.J. Ache Sensors and Actuators B, 7 (1992) 540-543.*

* cited by examiner

*Primary Examiner* — Robert J Hill, Jr.
*Assistant Examiner* — Dwan A Gerido
(74) *Attorney, Agent, or Firm* — Oblon, Spivak, McClelland, Maier & Neustadt, L.L.P.

(57) ABSTRACT

To provide a lead concentration determination reagent which realizes accurate, high-sensitivity, and simple-manner determination of the lead ion concentration (also referred to simply as "lead concentration") of a sample solution in the presence of calcium ions, and a lead concentration determination method employing the reagent. The lead concentration determination reagent contains (A) a water-soluble porphyrin derivative or a salt thereof, (B) at least one member selected from among polyacrylamide, polyvinyl alcohol, and polyethylene glycol, and (C) a calcium-ion-supplying compound.

11 Claims, 7 Drawing Sheets

US 8,133,739 B2

REAGENT FOR MEASUREMENT OF CONCENTRATION OF LEAD, AND METHOD FOR MEASUREMENT OF CONCENTRATION OF LEAD

TECHNICAL FIELD

The present invention relates to a reagent for determining lead concentration (hereinafter may be referred to as a "lead concentration determination reagent") employing a water-soluble porphyrin, and to a method for determining lead concentration (hereinafter may be referred to as "lead concentration determination method") by use of the reagent.

BACKGROUND ART

Lead, which has useful electrochemical properties such as conductivity and can be readily processed, is employed in a variety of industrial products, including solder, batteries, and glass materials. When these lead-containing products are discharged as municipal wastes and industrial wastes and incinerated in an incineration plant, in some cases, high-concentration lead is detected in the incineration ash and fly ash discharged from the plant. Although the discharged incineration ash and fly ash are subjected to landfill disposal, there are concerns about elution of lead by, for example, rainwater around the landfill sites. As has been known, lead itself is very poisonous, and even a trace amount of lead is strongly harmful to the human body, causing malfunction of the nervous system and lead-poisoning symptoms such as anemia, headache, inappetence, and lead colic. Therefore, standards for pollution control on landfill sites and the like have been established, and agents and methods for preventing elution of lead have been developed, along with lead assay methods for leachate. Furthermore, since lead is strongly harmful to many other living organisms, standards such as environmental quality standards and wastewater quality standards have been established with respect to lead. Meanwhile, there is demand for a simple lead assay method which can be applied to environmental analysis performed in a variety of fields.

Generally, lead concentration is determined through a method employing an atomic absorption photometer or an ICP emission spectrophotometer. Such a method requires feeding of acetylene gas or argon gas and provision of an exhaust duct, and involves cumbersome operation. Therefore, the method is not suited for routine on-site environmental analysis and routine analysis carried out on incineration sites.

Meanwhile, absorptiometry, which determines the concentration of a substance in a sample by use of a colorimetric reagent, can be performed by means of a small, inexpensive apparatus through simple operations. Therefore, absorptiometry is suited for simple assay. The colorimetric reagent employed in determination of lead concentration includes porphyrin derivatives such as water-soluble porphyrin and porphyrin nucleus-incorporated polymer. As has been known, by use of such a porphyrin derivative, a trace amount of lead contained in aqueous solution can be determined.

However, environmental analysis solution samples generally contain a variety of miscellaneous matters other than lead. These miscellaneous matters are possible interference substances in high-sensitivity and accurate lead assay. For example, calcium, which is always found in the environment (e.g., in sea water, river water, tap water, industrial wastewater, or ash leachate), is present in aqueous solution as a divalent ion, as is the case with lead. Thus, calcium may serve as an interference substance in determination of lead through absorptiometry based on chemical reaction between a colorimetric reagent and lead. Particularly, since ash leachate contains calcium at a concentration as high as several tens to several hundreds of mM, difficulty is encountered in determination of lead in ash leachate through absorptiometry employing water-soluble porphyrin as a colorimetric reagent. In order to determine, through absorptiometry, lead concentration of a sample solution containing calcium, a preliminary treatment (separation of calcium from lead, or masking of calcium) must be performed.

For separating calcium from lead, there may be employed a technique employing a chelate resin predominantly containing iminodiacetic acid, which has strong affinity to heavy metals, including lead. Thus, when a lead-containing sample solution is caused to pass through a column or filter filled with or formed of such a chelate resin, lead can be selectively captured. Then, the thus-captured lead is eluted through passage of an acidic eluent, and the lead concentration of the eluate is determined. This technique requires passage of an eluent in an accurate volume many times by means of a pump or syringe, making the technique cumbersome. Therefore, the technique is not suited for a simple assay technique.

Ethylenediaminetetraacetic acid (EDTA) and ethylene glycol bis(2-aminoethyl ether)tetraacetic acid (EGTA) are known calcium-masking agents. However, these masking agents also capture lead. In order to mask high-concentration calcium, a masking agent must be added at high concentration. In this case, lead that is present at a concentration considerably lower than that of calcium is thoroughly masked. Therefore, neither EDTA nor EGTA can be employed as a calcium-masking agent in determination of lead through absorptiometry employing water-soluble porphyrin.

For the absorptiometric determination of lead in a sample solution containing calcium as an interference component, there has been reported a lead concentration determination method in which such a solution is treated with an agent containing calcium added in advance thereto and a porphyrin nucleus-incorporated polymer (Patent Document 1). When the method is employed, interference of calcium can be eliminated. However, since preparation of the reagent involves a polymerization step, considerable time and cost are required. In addition, the porphyrin skeleton which has been incorporated into the polymer exhibits a broadened peak, reducing the determination sensitivity. Therefore, in an assay of microamount lead at the environmental quality standard level or wastewater quality standard level, there is further demand for enhancement of the sensitivity of the assay.

Patent Document 1: WO 2006/011549

DISCLOSURE OF THE INVENTION

Problems to be Solved by the Invention

Thus, an object of the present invention is to provide a lead concentration determination reagent which realizes accurate, high-sensitivity, and simple-manner determination of the lead ion concentration (hereinafter may also be referred to simply as "lead concentration") of a sample solution in the presence of calcium ions. Another object of the invention is to provide a lead concentration determination method employing the reagent.

Means for Solving the Problems

In view of the foregoing, the present inventor has carried out extensive studies, and has quite surprisingly found that, in lead concentration determination through absorptiometry employing a water-soluble porphyrin, interference by calcium ions can be effectively eliminated by use of a calcium-supplying compound, and a polymer selected from polyacrylamide, polyvinyl alcohol, and polyethylene glycol, in combination, whereby the lead concentration of a sample solution in the presence of calcium ions can be accurately assayed with high sensitivity and in a simple manner. The present invention has been accomplished on the basis of this finding.

Accordingly, the present invention provides a lead concentration determination reagent comprising (A) a water-soluble porphyrin derivative or a salt thereof, (B) at least one member selected from among polyacrylamide (hereinafter may be abbreviated as PAAm), polyvinyl alcohol (hereinafter may be abbreviated as PVA), and polyethylene glycol (hereinafter may be abbreviated as PEG), and (C) a calcium-ion-supplying compound.

The present invention also provides a method for determining lead concentration, comprising mixing a sample solution with the aforementioned lead concentration determination reagent to form a mixture, and measuring the absorbance of the mixture.

Effects of the Invention

The lead concentration determination reagent of the present invention realizes accurate determination of the lead concentration of a sample solution in the presence of calcium ions in a simple manner without interference by calcium ions. Thus, the reagent of the invention can serve as a useful lead concentration determination reagent for the assay of wastewater, discharged liquid, ash leachate, etc.

BEST MODES FOR CARRYING OUT THE INVENTION

Figure 1:
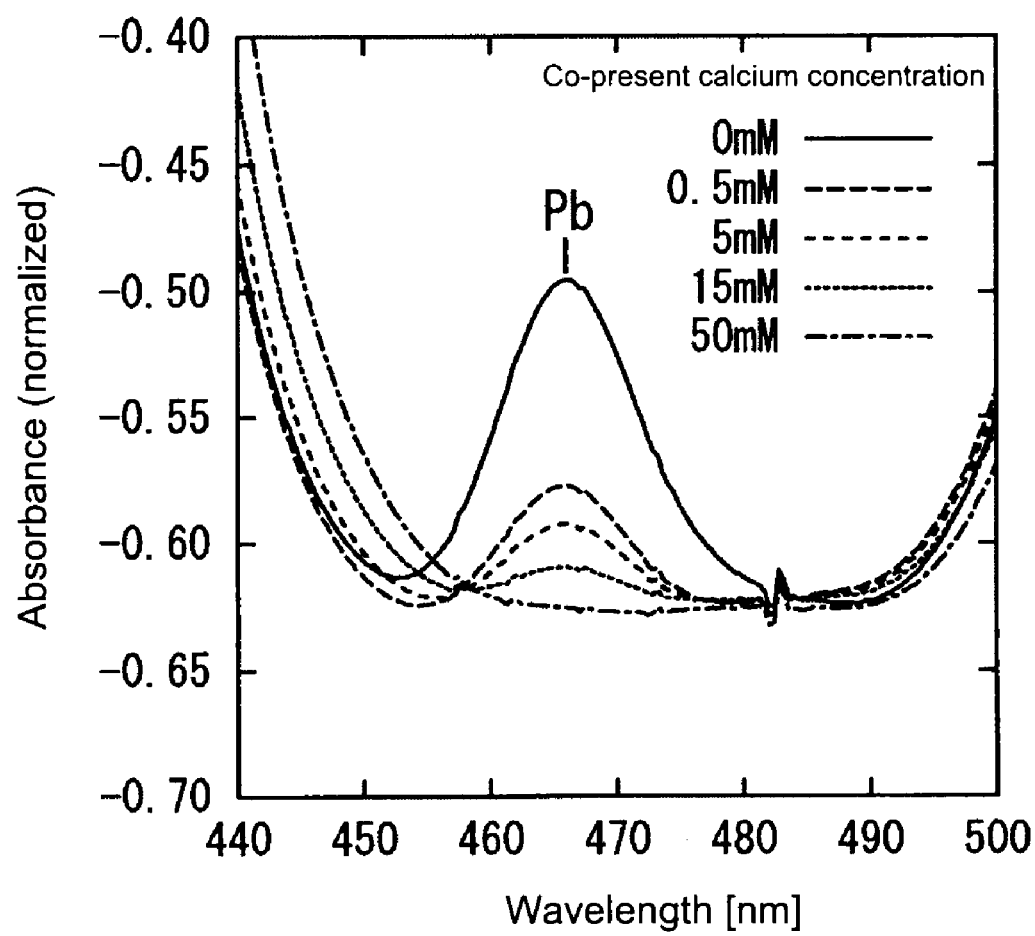
FIG. 1 Absorption spectra of reaction products between a sample solution (lead-0 to 50 mM calcium mixture) and TPPS.

The water-soluble porphyrin derivative or a salt thereof (A) employed in the present invention includes porphyrin compounds having a porphyrin skeleton and exhibiting change in absorbance of light having a specific wavelength upon reaction with a lead ion.

Specific examples of the porphyrin derivative include water-soluble porphyrins represented by the following formula (1):

[F1]

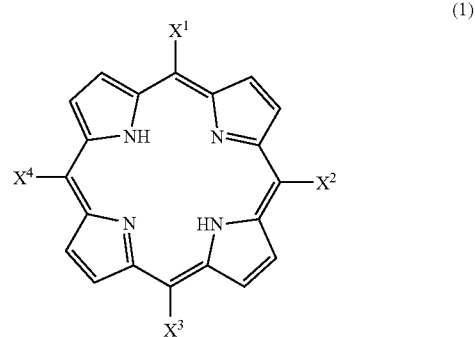

(1)

(wherein at least one of $X^1$ to $X^4$ represents any of the following groups:

[F2]

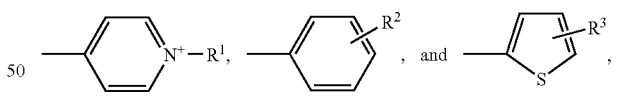

each of the rest of the group(s) represents a hydrogen atom, and $R^1$ represents an alkyl group, a sulfoalkyl group, a carboxyalkyl group, a hydroxyalkyl group, or a hydrogen atom; and each of $R^2$ and $R^3$ represents a hydroxyl group, a carboxyl group, an amino group, a sulfonic acid residue, a phosphoric acid residue, or a trialkylammonium group).

Examples of the alkyl group represented by $R^1$ in formula (1) include C1 to C6 alkyl groups such as methyl, ethyl, n-propyl, isopropyl, n-butyl, n-pentyl, and n-hexyl. Of these, methyl is particularly preferred. Examples of the sulfoalkyl group include sulfo-(C1 to C6) alkyl groups such as sulfomethyl, sulfoethyl, sulfopropyl, sulfobutyl, sulfopentyl, and sulfohexyl. Examples of the carboxyalkyl group include carboxy-(C1 to C6) alkyl groups such as carboxymethyl, carboxyethyl, carboxypropyl, carboxybutyl, carboxypentyl, and carboxyhexyl. Examples of the hydroxyalkyl group include hydroxy-(C1 to C6) alkyl groups such as hydroxymethyl, hydroxyethyl, hydroxypropyl, hydroxybutyl, hydroxypentyl, and hydroxyhexyl.

Specific examples of $R^2$ and $R^3$ include a hydroxyl group, a carboxyl group, an amino group, a sulfonic acid residue ($—SO_3H$), a phosphoric acid residue, and a trimethylammonium group. Among them, a sulfonic acid residue ($—SO_3H$) and a trimethylammonium group are particularly preferred.

Examples of preferred groups $X^1$ to $X^4$ include sulfophenyl, sulfothienyl, trimethylammoniumphenyl, hydroxyphenyl, carboxyphenyl, aminophenyl, phosphorylphenyl, pyridinium, methylpyridinium, sulfoethylpyridinium, carboxymethylpyridinium, and hydroxyethylpyridinium. Examples of more preferred such groups include 4-sulfophenyl, 4-sulfothienyl-2-yl, 4-trimethylammoniumphenyl, 4-hydroxyphenyl, 4-carboxylphenyl, 4-aminophenyl, 4-phosphorylphenyl, N-methylpyridinium-4-yl, N-methylpyridinium-3-yl, and N-sulfoethylpyridinium-4-yl. Examples of even more preferred such groups include 4-sulfophenyl, 4-trimethylammoniumphenyl, N-methylpyridinium-4-yl, and N-methylpyridinium-3-yl.

Examples of particularly preferred compounds represented by formula (1) include 5,10,15,20-tetrakis(4-sulfophenyl)porphyrin (hereinafter may be abbreviated as TPPS), 5,10,15,20-tetrakis(N-methylpyridinium-4-yl)porphyrin (hereinafter may be abbreviated as TMPyP), and 5,10,15,20-tetrakis(4-trimethylammoniumphenyl)porphyrin. Of these, TPPS and TMPyP are preferred, from the viewpoint of measurement sensitivity.

The water-soluble porphyrin derivative of the present invention represented by formula (1) may be in the salt form in accordance with the type of substituents $X^1$ to $X^4$. Specific examples of the salt include acid-added salts such as hydrochlorides, sulfates, nitrates, and p-toluenesulfonates.

Water-soluble porphyrins represented by formula (I) employed in the present invention are already known as colorimetric reagents for the determination of trace metal elements. Such a porphyrin derivative may be produced through, for example, forming tetraphenylporphyrin through dehydration-condensation of pyrrol and benzaldehyde and oxidation with p-chloranil, and sulfonating the phenyl groups of the tetraphenylporphyrin in concentrate sulfuric acid (J. S. Lindsey, I. C. Schreiman, H. C. Hsu, P. C. Kearney, and A. M. Marguerettaz, "Rothemund and Adler-Longo Reactions Revisited: Synthesis of Tetraphenylporphyrins under Equilibrium Conditions," J. Org. Chem., 1987, 52, 827). Alternatively, these compounds may also be available as commercial products.

The lead concentration determination reagent preferably contains the water-soluble porphyrin represented by formula (1) in an amount of 0.01 to 1,000 µmol/L (upon use), more preferably 0.1 to 500 µmol/L, particularly preferably 1 to 100 µmol/L, from the viewpoint of accuracy of determination of lead contained in a trace amount in a sample solution.

The ingredient (B) employed in the present invention is polyacrylamide (PAAm), polyvinyl alcohol (PVA), or polyethylene glycol (PEG). Among these polymers, polyacrylamide is preferred from the viewpoints of measurement sensitivity and stability. These polymers, which are water-soluble, are known compounds which find a variety of uses, and commercially available.

The lead concentration determination reagent of the present invention preferably has a PAAm concentration (upon use) of 1 to 40 mass %, particularly preferably 10 to 25 mass %. The PAAm preferably has an average molecular weight of 1,000 to 100,000, particularly preferably 5,000 to 20,000.

The lead concentration determination reagent of the present invention preferably has a PVA concentration (upon use) of 0.1 to 20 mass %, particularly preferably 1 to 10 mass %. The PVA preferably has a polymerization degree of 100 to 10,000, particularly preferably 200 to 2,000.

The lead concentration determination reagent of the present invention preferably has a PEG concentration (upon use) of 0.1 to 20 mass %, particularly preferably 1 to 10 mass %. The PEG preferably has a molecular weight of 100 to 50,000, particularly preferably 10,000 to 40,000.

Generally, PAAm is employed as a paper strengthening agent, an adhesive, a coagulant, and a cosmetic base for providing a cosmetic with appropriate viscosity and stability. PAAm gel is employed in electrophoresis. PVA is employed as an adhesive, a surfactant, a film material, etc. PEG is employed as a stabilizer or a base for drugs and other materials. However, there has never been known use of PAAm, PVA, or PEG as a masking agent for calcium ions or as an additive for establishing stable reaction between water-soluble porphyrin and lead ions.

No particular limitation is imposed on the calcium-ion-supplying compound for releasing calcium ions (ingredient (C)) employed in the lead concentration determination reagent of the present invention, so long as the compound releases calcium ions and does not impair the effects of the present invention. Examples of the calcium-ion-supplying compound include inorganic calcium salts such as calcium chloride, calcium sulfate, calcium nitrate, calcium carbonate, calcium hydroxide, calcium hydrogenphosphate, and calcium phosphate; and organic calcium salts such as calcium acetate, calcium formate, calcium lactate, calcium gluconate, calcium benzaoate, calcium isobutyrate, calcium propionate, and calcium salicylate. The calcium-ion-supplying compound is preferably an inorganic calcium salt; e.g., calcium chloride, calcium sulfate, or calcium nitrate, with calcium chloride being particularly preferred.

The lead concentration determination reagent of the present invention preferably contains the calcium-ion-supplying compound in such an amount (upon use) that calcium ions are supplied at a concentration of 0.1 to 100 mmol/L, particularly preferably 5 to 50 mmol/L.

So long as the effects of the present invention are not impaired, the lead concentration determination reagent of the present invention may contain, in addition to the aforementioned ingredients and water, an optional ingredient employed for determining heavy metal ions in an ordinary solution. Examples of the optional ingredient include a pH-regulating agent, a surfactant, an antioxidant, a preservative, and a masking agent for other metals.

Examples of the pH-regulating agent include at least one compounds selected from among N-cyclohexyl-3-aminopropanesulfonic acid (hereinafter may be abbreviated as CAPS), N-cyclohexyl-2-aminoethanesulfonic acid, sodium hydrogencarbonate, sodium carbonate, sodium hydroxide, etc. Preferably, the pH-regulating agent controls the pH of the mixture of the lead concentration determination reagent and a sample to 8 to 13, more preferably 9 to 11 (25° C.)

Examples of the surfactant include a cationic surfactant, an anionic surfactant, and a non-ionic surfactant.

Examples of the masking agent for other metals include ethylenediamine-N,N'-dipropionic acid, ethylenediamine-N,N'-diacetic acid, and 1,6-diaminohexane-N,N,N',N'-tetraacetic acid.

The lead concentration determination reagent of the present invention may be in any form of non-treated liquid, concentrate, powder, paste, etc. The ingredients of the lead concentration determination reagent may be appropriately stored separately or as a mixture.

The method of the present invention for determining lead concentration is carried out by mixing the aforementioned lead concentration determination reagent with a sample solution to form a mixture and determining the absorbance of the mixture.

Upon determination, the pH of the mixture of the lead concentration determination reagent and a sample solution is preferably controlled to 8 to 13, more preferably 9 to 11 (25° C.). When the mixture has a pH falling outside the pH range, the pH of the lead concentration determination reagent is preferably adjusted with a pH-regulating agent in advance to fall within the pH range.

Before measurement of absorbance, reaction between the mixture of the reagent and the sample solution is preferably promoted sufficiently by, for example, heating the mixture. The heating temperature is preferably 30 to 90° C., and the heating time is preferably 1 to 60 min. From the viewpoints of accuracy, sensitivity, and throughput, particularly preferably, the heating temperature is 60 to 80° C., and the heating time is 3 to 15 min.

Determination of the lead concentration of a sample solution by use of the lead concentration determination reagent of the present invention may be performed through, for example, absorptiometry with a calibration curve obtained by use of a standard sample.

The absorbance of a sample is preferably measured at a wavelength of 350 to 700 nm, more preferably 400 to 500 nm, particularly preferably 460 to 490 nm, by means of an absorptiometer.

No particular limitation is imposed on the sample whose lead concentration is determined in the present invention. Examples of the sample include environmental samples such as sea water, river water, tap water, industrial wastewater, and ash (e.g., incineration ash or incineration fly ash) leachate; foods and beverages; agricultural and marine products; plants; drugs; body fluid samples (human and animals) such as blood, saliva, and sperm; organs (human and animals) such as kidney, heart, and brain; and biomaterial samples (human and animals) such as muscle, skin, nerve tissue, hair, and feces.

In the lead concentration determination method employing the lead concentration determination reagent of the present invention, examples of the sample solution include non-treated liquids of a sample, and extracts, concentrates, dilutes, etc. of the sample for determination obtained through appropriate known techniques of extraction, concentration, dilution, etc. No particular limitation is imposed on the calcium ion concentration of the sample solution, and it is preferably 150 mM or less, particularly preferably 50 mM or less.

EXAMPLES

The present invention will next be described in more detail by way of examples, which should not be construed as limiting the invention thereto.

Referential Example 1

Lead Concentration Determination Reagent A Containing only TPPS

Preparation of Lead Concentration Determination Reagent

An aqueous solution (pH: 10) containing TPPS (50 μM) serving as a water-soluble porphyrin and CAPS (180 mM) serving as a pH-regulating agent was prepared. This solution was employed as lead concentration determination reagent A.

Preparation of sample solutions and standard samples

Lead-calcium-containing aqueous solutions containing lead (0.15 mg/L) and calcium chloride (0.5, 5, 15, 50, and 150 mM) and having a pH within the range of 9 to 12.5 were provided as sample solutions. In order to draw calibration curves, lead-containing standard solutions (lead concentration: 0 and 0.15 mg/L) were provided as standard samples.

Determination of Lead Concentration

Lead concentration determination reagent A (250 μL) was mixed with each sample solution (250 μL), and the mixture was heated at 75° C. for five minutes. The absorption spectrum of the thus-treated mixture was measured by means of a spectrophotometer.

The obtained absorption spectrum was normalized, to thereby eliminate base-line-related variations. In a similar manner, the absorption spectrum of each standard sample was measured instead of those of the sample solutions.

Through comparison of the absorption spectrum of the mixture containing one standard sample with that of the mixture containing the other standard sample, a clear change in absorbance attributed to reaction of TPPS with lead was observed at a measurement wavelength of about 470 nm. A calibration curve was drawn from the measurements at the wavelength. With reference to the calibration curve, the lead concentration of each sample solution was estimated from the absorbance of the mixture of the sample solution and reagent A.

Figure 2:
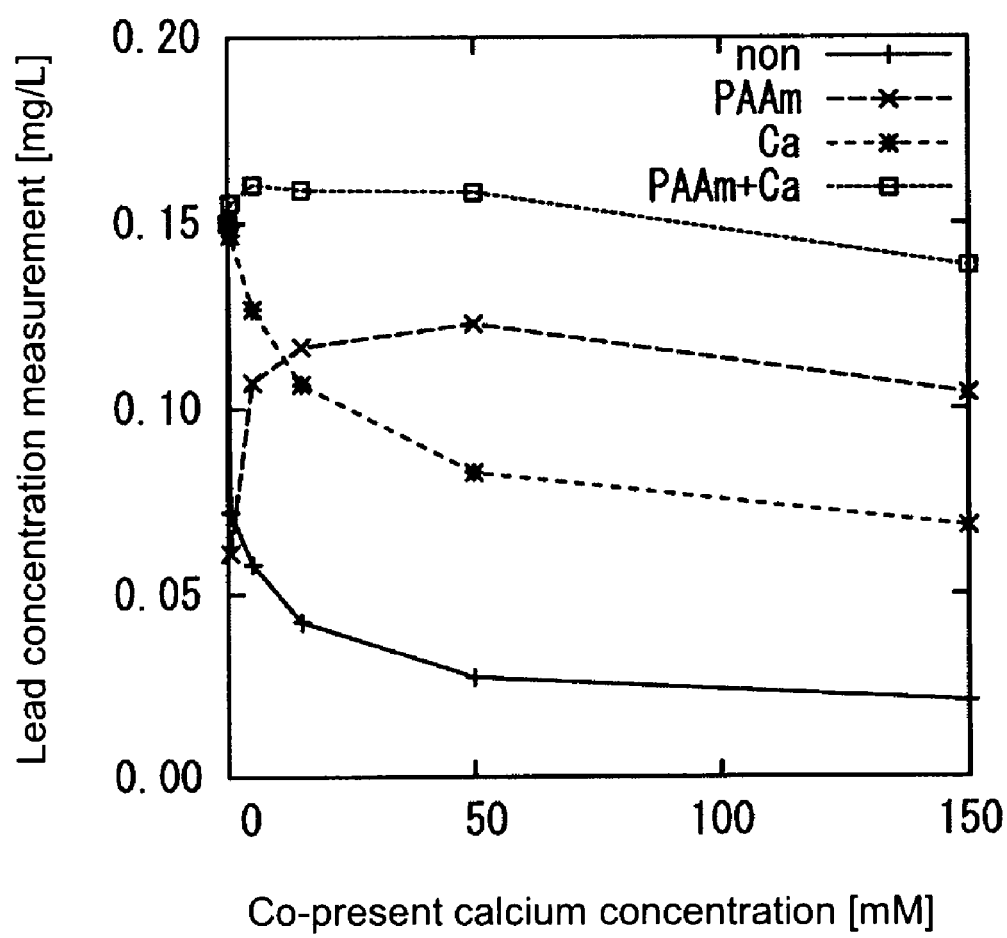
FIG. 2 Absorption spectra of reaction products between a sample solution (lead-0 to 150 mM calcium mixture) and TPPS (non), between the aforementioned sample solution and TPPS and PAAm (PAAm), between the aforementioned sample solution and TPPS and a calcium-supplying compound (Ca), and between the aforementioned sample solution and TPPS, PAAm, and a calcium-supplying compound (PAAm+Ca).

FIG. 1 shows absorption spectra of sample solutions after reaction with lead concentration determination reagent A containing only TPPS. Peaks attributed to lead were observed at about 466 nm. However, even under the same lead concentration, when co-present calcium concentration increased, the peak height decreased, and eventually no peak was observed. Lead concentrations calculated from the data of FIG. 1 were plotted with respect to co-present calcium concentrations, and the obtained graph is shown in FIG. 2 (non: reference). As is clear from FIG. 2, the lead concentration measurement determined in the presence of calcium even in a very small amount was lower than the true lead concentration (0.15 mg/L). Thus, the presence of calcium was found to impede accurate lead determination.

Test Example 1

Lead Concentration Determination Reagents B1 to B3 Containing TPPS (Ingredient (A)) and PAAm (Additive, Ingredient (B)) and/or Calcium Chloride (Additive, Ingredient (C))

Preparation of Lead Concentration Determination Reagent

Aqueous solutions (pH: 10) each containing polyacrylamide (additive) (average molecular weight: 10,000) (20 mass %) and/or calcium chloride (additive) (10 mM), a water-soluble porphyrin (TPPS) (50 μM), and a pH-regulating agent (CAPS) (180 mM) were prepared. The solutions were employed as lead concentration determination reagents B1 to B3. Reagent B1 contained only polyacrylamide as an additive; reagent B2 contained only calcium chloride as an additive; and reagent B3 contained polyacrylamide and calcium chloride in combination.

Preparation of Sample Solutions and Standard Samples

The same samples as employed in Referential Example 1 were employed.

Determination of Lead Concentration

The procedure of Referential Example 1 was repeated, except that reagents B1 to B3 were used instead of lead concentration determination reagent A.

FIG. 2 also shows the results of determination of lead concentration in the case where lead concentration determination reagents B1 to B3 were employed. When reagent B1 containing only polyacrylamide as an additive was used, interference by high-concentration co-present calcium was mitigated to a certain degree. However, when low-concentration (about 15 mM or lower) calcium was co-present, lead concentration measurements are likely to be estimated lower. When reagent B2 containing calcium as an additive was used, the lead concentration measurements monotonously decreased in response to the co-present calcium concentration, which is similar to the additive-free case. In contrast, when reagent B3 containing both polyacrylamide and calcium chloride was used, virtually true lead concentrations were obtained through calculation, even when calcium was present over a low to high concentration range.

Test Example 2

Lead Concentration Determination Reagent C Containing TPPS (Ingredient (A)), PVA (Additive, ingredient (B)), and Calcium Chloride (Additive, Ingredient (C)), and Lead Concentration Determination Reagent D Containing TPPS (Ingredient (A)), PEG (Additive, Ingredient (B)), and Calcium Chloride (Additive, Ingredient (C))

Preparation of Lead Concentration Determination Reagent

An aqueous solution (pH: 10) containing PVA (additive) (polymerization degree: 500) (2.5 mass %), calcium chloride (additive) (10 mM), a water-soluble porphyrin (TPPS) (50 µM), and a pH-regulating agent (CAPS) (180 mM) was prepared. The solution was employed as lead concentration determination reagent C.

Separately, an aqueous solution (pH: 10) containing PEG (additive) (average molecular weight: 20,000) (5 mass %), calcium chloride (additive) (10 mM), a water-soluble porphyrin (TPPS) (50 µM), and a pH-regulating agent (CAPS) (180 mM) was prepared. The solution was employed as lead concentration determination reagent D.

The procedure of Test Example 1 was repeated, except that the aforementioned lead concentration determination reagent B3 was changed to reagent C or reagent D.

Figure 3:
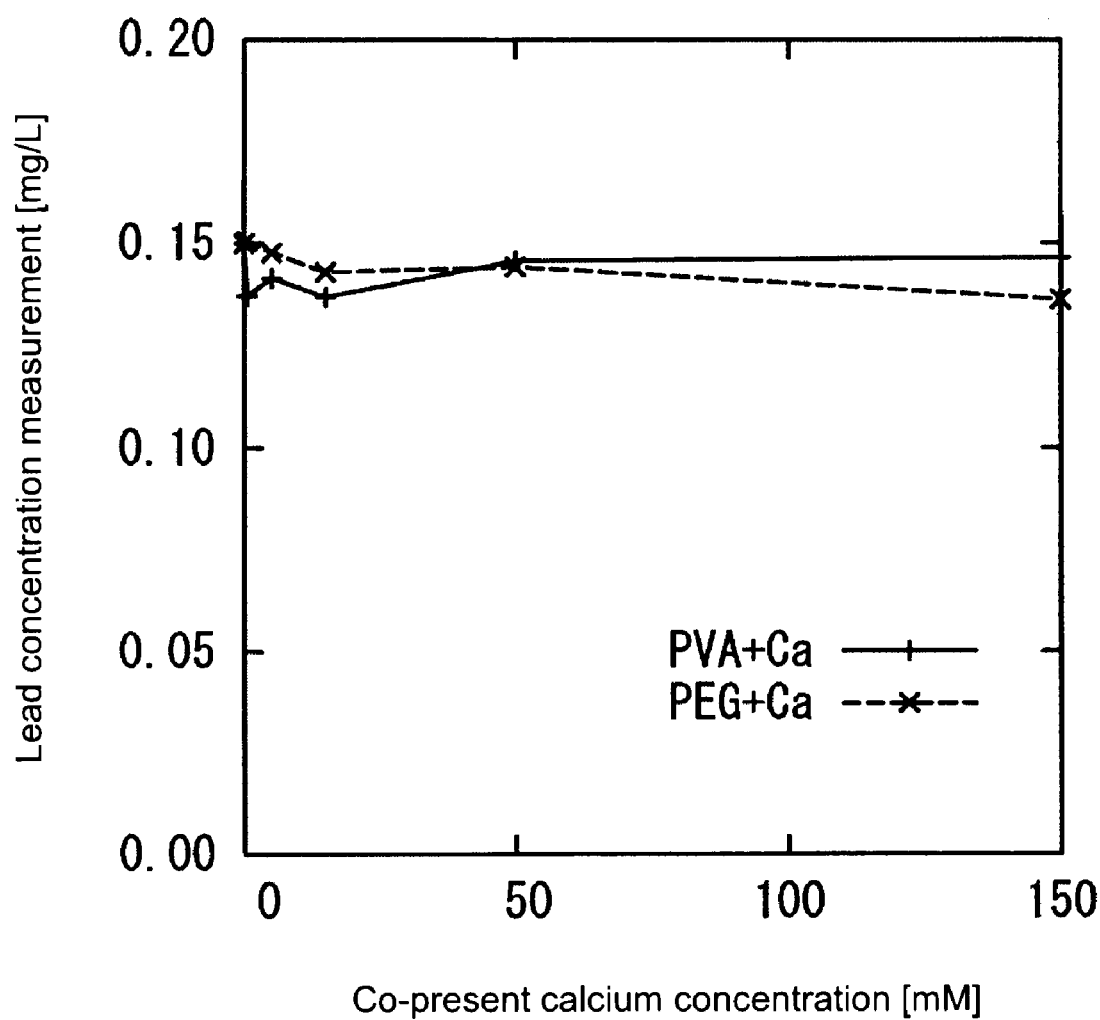
FIG. 3 Absorption spectra of reaction products between a sample solution (lead-0 to 150 mM calcium mixture) and TPPS, PVA, and a calcium-supplying compound (PVA+Ca), between the aforementioned sample solution and TPPS, PEG, and a calcium-supplying compound (PEG+Ca).

FIG. 3 shows the results of determination of lead concentration in the case where lead concentration determination reagent C containing PVA and calcium chloride in combination was employed, and the results of determination of lead concentration in the case where lead concentration determination reagent D containing PEG and calcium chloride in combination was employed. In either case (use of lead concentration determination reagent C or D), virtually true lead concentrations were obtained through calculation without decrease in concentration measurements, even when co-present calcium increased.

Referential Example 2

Lead Concentration Determination Reagents E and F Containing TPPS (Ingredient (A)) and a Masking Agent (EDTA or EGTA)

An aqueous solution (pH: 10) containing a water-soluble porphyrin (TPPS) (50 µM), a pH-regulating agent (CAPS) (180 mM), and EDTA or EGTA (50 mM) was prepared. The solution was employed as lead concentration determination reagent E or F, respectively. EDTA and EGTA are known as calcium chelating agents (masking agents) generally employed in the art. The EDTA concentration and the EGTA concentration were adjusted to 50 mM so that several tens of mM or more of calcium can be masked.

The procedure of Referential Example 1 was repeated, except that reagent A was changed to reagent E or F.

Figure 4:
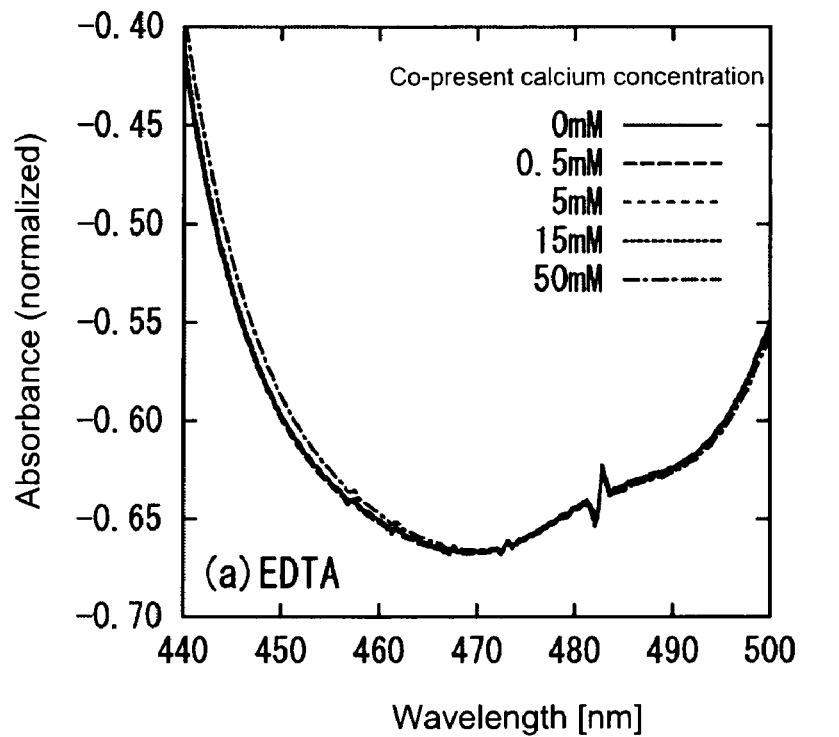
FIG. 4 (a) Absorption spectra of reaction products between a sample solution (lead-0 to 50 mM calcium mixture) and TPPS, EDTA, and a calcium-supplying compound. (b) Absorption spectra of reaction products between a sample solution (lead-0 to 50 mM calcium mixture) and TPPS, EGTA, and a calcium-supplying compound.
Figure 4:
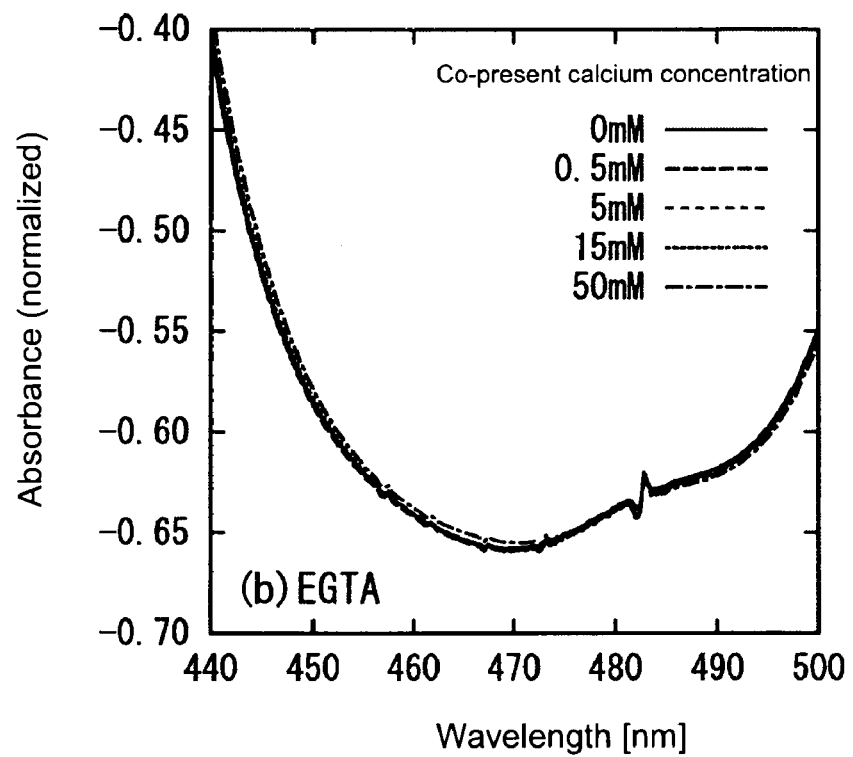

FIGS. 4(a) and 4(b) show absorption spectra of mixtures of a sample and lead concentration determination reagent E or F. In the case where either EDTA or EGTA was employed, no peak attributed to lead was observed at any calcium concentration. One possible reason for the disappearance of the peak is that EDTA or EGTA, having affinity to both calcium ions and lead ions and contained in a large excessive amount with respect to lead concentration (70,000 times or slight lower (ratio by mole)), captures almost all lead ions, thereby failing to form a lead-porphyrin complex. Therefore, in determination of the lead concentration of a sample solution containing calcium at high concentration through absorptiometry employing water-soluble porphyrin, neither EDTA nor EGTA was able to be employed as a calcium-masking agent.

Test Example 3

Lead Concentration Determination Reagents G1 to G4 Containing TMPyP (Ingredient (A)) and PAAm (Additive, Ingredient (B)) and Calcium Chloride (Additive, Ingredient (C))

Preparation of Lead Concentration Determination Reagent

Aqueous solutions (pH: 10) each containing a water-soluble porphyrin (TMPyP) (50 µM), polyacrylamide (additive) (average molecular weight: 10,000) (20 mass %) and/or calcium chloride (additive) (30 mM), and a pH-regulating agent (CAPS) (180 mM) were prepared. The solutions were employed as lead concentration determination reagents G1 to G4. Reagent G1 contained no polyacrylamide or calcium chloride; reagent G2 contained only polyacrylamide as an additive; reagent G3 contained only calcium chloride as an additive; and reagent G4 contained polyacrylamide and calcium chloride in combination.

Preparation of Sample Solutions and Standard Samples

The same samples as employed in Referential Example 1 were employed.

Determination of Lead Concentration

The procedure of Referential Example 1 was repeated, except that reagents G1 to G4 were used instead of lead concentration determination reagent A.

Through comparison of the absorption spectrum of the mixture containing one standard sample with that of the mixture containing the other standard sample, a clear change in absorbance attributed to reaction of TMPyP with lead was observed at a measurement wavelength of about 480 nm. The wavelength was employed as a measurement wavelength.

Figure 5:
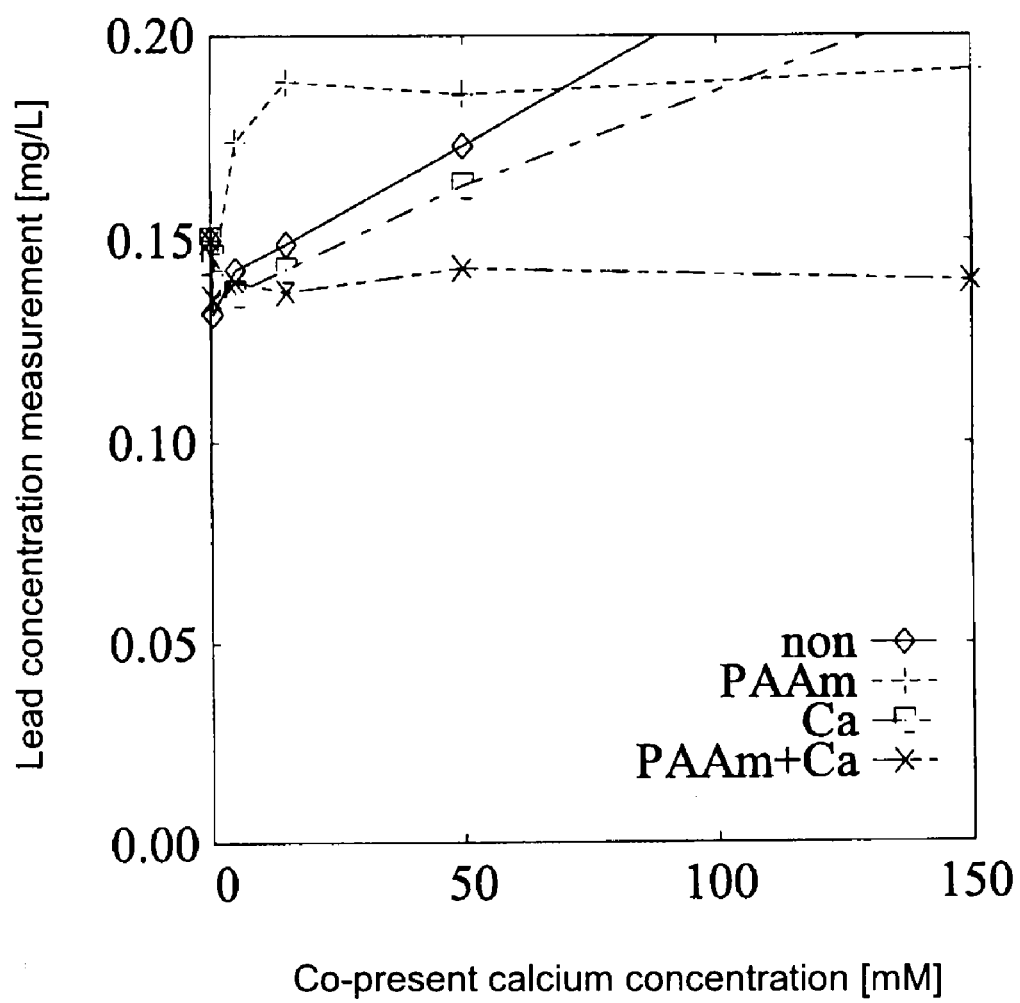
FIG. 5 Absorption spectra of reaction products between a sample solution (lead-0 to 150 mM calcium mixture) and TMPyP (non), between the aforementioned sample solution and TMPyP and PAAm (PAAm), between the aforementioned sample solution and TMPyP and a calcium-supplying compound (Ca), and between the aforementioned sample solution and TMPyP, PAAm, and a calcium-supplying compound (PAAm+Ca).

FIG. 5 shows the results of determination. When reagent G1 containing no additive was used, the lead concentration measurements involved positive errors due to the presence of calcium in each sample solution. A similar tendency was observed when reagent G3 containing only calcium chloride as an additive was used. When reagent G2 containing only polyacrylamide as an additive was used, the lead concentration measurements involved positive errors due to the presence of low-concentration calcium in each sample solution. However, when the co-present calcium concentration of a sample was about 15 mM or higher, the measurements were constant. In contrast, when reagent G4 containing both polyacrylamide and calcium was used, virtually true lead concentrations were obtained, even when calcium was co-present in a sample over a low to high concentration range.

Test Example 4

Comparison of the Reagent of the Invention with Porphyrin Nucleus-Incorporated Polymer For the determination of the lead concentration in a sample solution containing calcium at high concentration, there has been reported a determination method employing a porphyrin-polymer-containing lead concentration determination reagent, the polymer being a porphyrin nucleus-incorporated polymer serving as a colorimetric reagent (WO 2006/011549). The case where lead concentration was determined by means of a handy lead concentration meter through employment of a porphyrin-polymer-containing lead concentration determination reagent as a colorimetric reagent was compared with the case where lead concentration was determined by means of a handy lead concentration meter through employment of the lead concentration determination reagent of the present invention.

The handy lead concentration meter includes a main body holding a small-scale spectrophotometer and a heater for heating cells, and a personal computer attached thereto, and determines lead concentration through absorptiometry. In an assay, a mixture of a lead concentration determination reagent and a sample solution is placed in a cuvette. The cuvette is set in the apparatus, and the measurement is started. An absorption spectrum at the start of the measurement is obtained, and another absorption spectrum is measured after heating of the sample at 75° C. for five minutes. The two spectra are normalized and then, differentiated, to thereby obtain a difference spectrum. Since the peak height of the difference spectrum at 466 nm varies in response to the lead concentration, this peak height is employed as a signal. With reference to a calibration curve which has been obtained from standard samples having known concentrations, the relevant lead concentration is calculated and displayed by the concentration meter.

In Test Example 4, the aforementioned lead concentration determination reagent B3 was employed as the lead concentration determination reagent of the present invention.

The porphyrin-polymer-containing lead concentration determination reagent was also provided as a reference reagent. The synthesis of porphyrin nucleus-incorporated polymer and preparation of the reagent were performed in accordance with the description of WO 2006/011549. The calcium chloride concentration of the reagent was adjusted to 14 mM, and the polymer concentration was adjusted such that the absorbance of a 2-fold-diluted solution thereof exhibits an absorbance at 466 nm of 0.6 to 0.7.

Preparation of Sample Solutions and Standard Samples

The same materials as employed in Referential Example 1 were used. In order to draw a calibration curve and calculate the lower detection limit, aqueous lead solutions (0 to 0.1 mg/L) were employed.

The lead concentration determination reagent of the present invention or the porphyrin-polymer-containing lead concentration determination reagent (500 μL) was mixed with a sample solution (500 μL), and the mixture was subjected to lead concentration determination by means of a handy lead concentration meter.

Figure 6:
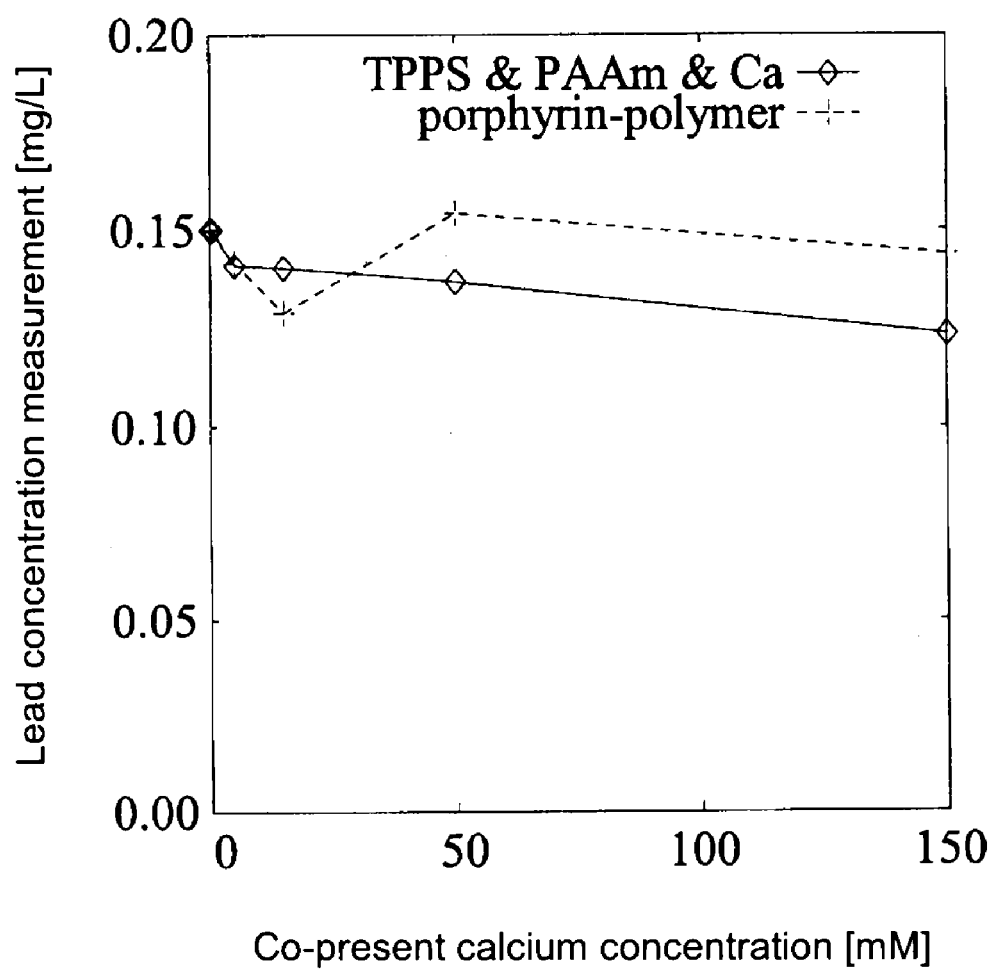
FIG. 6 Absorption spectra of reaction products between a sample solution (lead-0 to 150 mM calcium mixture) and (a) a lead concentration determination reagent (TPPS+PAAm+Ca) falling within the scope of the present invention, and between the sample solution and (b) a lead concentration determination reagent (porphyrin polymer) (reference), analyzed by means of a handy lead concentration meter.

FIG. 6 shows the results of determination. As is clear from FIG. 6, even when high-concentration calcium was co-present, virtually true lead concentrations were obtained through calculation, without considerable variation in lead concentration measurements.

Figure 7:
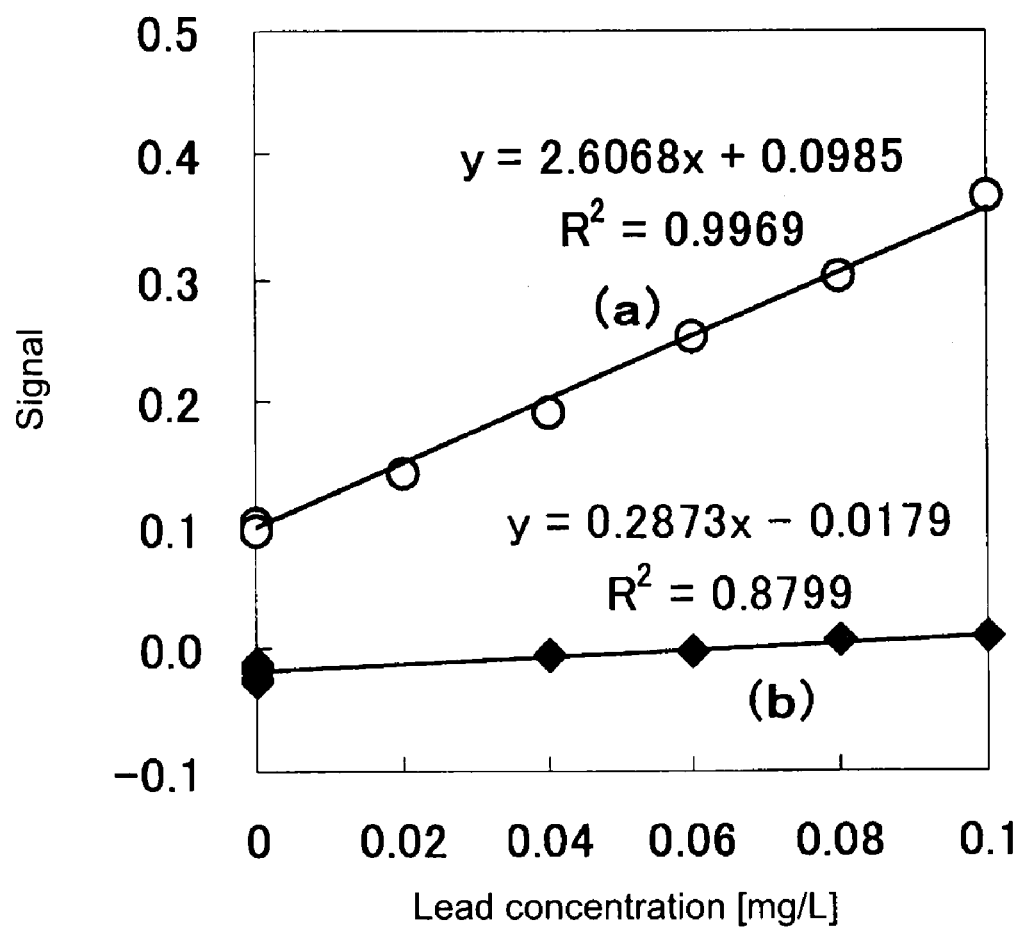
FIG. 7 Calibration curves of the cases in which reaction products between a sample solution (0 to 0.1 mg/L aq. lead solution) and (a) a lead concentration determination reagent (TPPS+PAAm+Ca) falling within the scope of the present invention, and between the sample solution and (b) a lead concentration determination reagent (porphyrin polymer) (reference), analyzed by means of a handy lead concentration meter.

FIG. 7 shows the relationship between lead concentration and signal (calibration curves) when the signal was measured at various lead concentrations. The reagent of the present invention provided a correlation factor R of 1.00, which is an excellent value. The calibration curve obtained from the reagent of the invention was found to have a large gradient, indicating that the reagent of the invention provided high lead detection sensitivity. Provided that the lead concentration at which a signal of three times the variation (standard deviation) at a lead concentration of 0 was obtained was regarded as a lower detection limit of lead concentration, the lower detection limit of assay by use of the lead concentration determination reagent of the present invention was estimated to be 0.006 mg/L, and that of assay by use of the porphyrin-polymer-containing lead concentration determination reagent was estimated to be 0.05 mg/L. With respect to lead, the standard for pollution control on a landfill site (as lead concentration of leachate), wastewater quality standard, and environmental quality standard have been established as 0.3, 0.1, and 0.01 mg/L, respectively. Therefore, the lead concentration determination reagent of the present invention can be employed not only for the assessment of the standard for pollution control on the landfill site and the wastewater quality standard, but also for the assessment of the environmental quality standard.

The invention claimed is:

1. A reagent for determining lead concentration in a sample solution in the presence of calcium ions comprising (A) a water-soluble porphyrin derivative or a salt thereof represented by formula (1):

[F1]

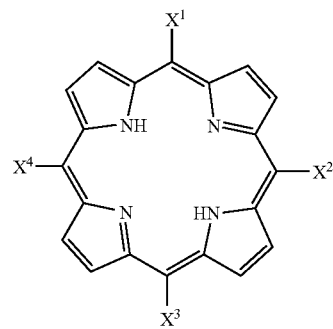

(1)

wherein at least one of $X^1$ to $X^4$ represents any of the following groups:

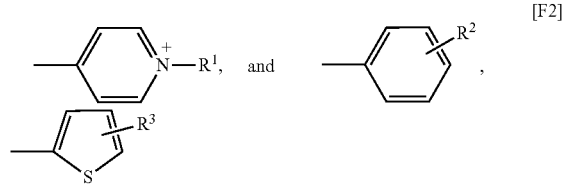

[F2]

each of the rest of the group(s) represents a hydrogen atom, and $R^1$ represents an alkyl group, a sulfoalkyl group, a carboxyalkyl group, a hydroxyalkyl group, or a hydrogen atom; and each of $R^2$ and $R^3$ represents a hydroxyl group, a carboxyl group, an amino group, a sulfonic acid residue, a phosphoric acid residue, or a trialkylammonium group, (B) at least one member selected from among polyacrylamide, polyvinyl alcohol, and polyethylene glycol, and (C) a calcium-ion-supplying compound.

2. A reagent for determining lead concentration according to claim 1, wherein (B) comprises at least one member selected from among 1 to 40 mass % of polyacrylamide, 0.1 to 20 mass % of polyvinyl alcohol, and 0.1 to 20 mass % of polyethylene glycol.

3. A reagent for determining lead concentration according to claim 1, wherein (B) is polyacrylamide.

4. A reagent for determining lead concentration according to claim 1, wherein (C) supplies calcium ions at a concentration of 0.1 to 100 mmol/L.

5. A reagent for determining lead concentration according to claim 1, wherein (C) is calcium chloride.

6. A reagent for determining lead concentration according to claim 1, which further comprises a pH-regulating agent for adjusting the pH thereof to from 8 to 13.

7. A reagent for determining lead concentration according to claim 1, wherein (A) is at least one water-soluble porphyrin selected from the group consisting of 5,10,15,20-tetrakis(4-sulfophenyl)porphyrin, 5,10,15,20-tetrakis(N-methylpyridinium-4-yl)porphyrin, and 5,10,15,20-tetrakis(4-trimethylammoniumphenyl)porphyrin.

8. A reagent for determining lead concentration according to claim 1, wherein the reagent comprises the water-soluble porphyrin in an amount of from 1 to 100 µmol/L.

9. A method for determining lead concentration, comprising mixing a sample solution in the presence of calcium ions with a reagent for determining lead concentration as recited in claim 1 to form a mixture, and measuring the absorbance of the mixture.

10. The method for determining lead concentration according to claim 9, wherein the pH of the mixture of the lead concentration determination reagent and the sample solution is from 8 to 13.

11. A method for determining lead concentration according to claim 9, wherein the absorbance of the sample is measured at a wavelength of from 460 to 490 nm.

* * * * *